United States Patent [19]
Johnson et al.

[11] Patent Number: 5,549,686
[45] Date of Patent: Aug. 27, 1996

[54] KNEE PROSTHESIS HAVING A TAPERED CAM

[75] Inventors: Todd S. Johnson, Fort Wayne; Kevin M. Greig, Leesburg, both of Ind.

[73] Assignee: Zimmer, Inc., Warsaw, Ind.

[21] Appl. No.: 254,210

[22] Filed: Jun. 6, 1994

[51] Int. Cl.$^6$ .................................................. A61F 2/64
[52] U.S. Cl. ............................................................ 623/20
[58] Field of Search ...................................... 623/18, 20

[56] References Cited

U.S. PATENT DOCUMENTS

| | | |
|---|---|---|
| 4,209,861 | 7/1980 | Walker et al. . |
| 4,213,209 | 7/1980 | Insall et al. . |
| 4,224,697 | 9/1980 | Murray et al. . |
| 4,249,270 | 2/1981 | Bahler et al. . |
| 4,298,992 | 11/1981 | Burstein et al. . |
| 4,353,136 | 10/1982 | Polyzoides et al. . |
| 4,634,444 | 1/1987 | Noiles ................................ 623/20 |
| 4,714,474 | 12/1987 | Brooks, Jr. et al. ................ 623/20 |
| 4,888,021 | 12/1989 | Forte et al. ........................ 623/20 |
| 4,892,547 | 1/1990 | Brown ................................ 623/20 |
| 4,950,297 | 8/1990 | Elloy et al. ........................ 623/20 |
| 4,950,298 | 8/1990 | Gustilo et al. .................... 623/20 |
| 4,959,071 | 9/1990 | Brown et al. ...................... 623/20 |
| 5,007,933 | 4/1991 | Sidebotham et al. ............. 623/20 |
| 5,011,496 | 4/1991 | Forte et al. ........................ 623/20 |
| 5,116,376 | 5/1992 | May .................................... 623/20 |
| 5,147,405 | 9/1992 | Van Zile et al. ................... 623/20 |
| 5,152,796 | 10/1992 | Slamin ............................... 623/20 |
| 5,181,925 | 1/1993 | Houston et al. ................... 623/20 |
| 5,236,461 | 8/1993 | Forte ................................... 623/20 |
| 5,330,534 | 7/1994 | Herrington et al. .............. 623/20 |
| 5,370,699 | 12/1994 | Hood et al. ........................ 623/20 |

FOREIGN PATENT DOCUMENTS

| | | |
|---|---|---|
| 0103697A1 | 3/1984 | European Pat. Off. . |
| 0294298 | 12/1988 | European Pat. Off. ............ 623/20 |
| 2701387 | 8/1994 | France ................................ 623/20 |

OTHER PUBLICATIONS

The Genesis Total Knee System—Smith & Nephew Richards—No date available.
Orthomet, Inc.—The Orthomet Axiom™ Total Knee—1993—JBJS, Jan. 1993.
Johnson & Johnson Orthopaedics Ltd.—The PFC Modular Total Knee System—British JBJS, Jan. 1991.

*Primary Examiner*—Mary Beth Jones
*Assistant Examiner*—Bruce E. Snow

[57] ABSTRACT

A knee joint prosthesis includes femoral and tibial components. The femoral component has a cam located near the upper extreme of the posterior condyles and substantially flush with the inside surface of the posterior condyles. The prosthesis is characterized by low cam and spine contact which reduces the stress on the components and improves their subluxation resistance. The tibial component has a posteriorly located spine to engage the femoral cam and a relief groove to accommodate the femoral cam. This allows the cam to remain low on the tibial spine and even go below the edges of the tibial component. Cam chamfers, where the femoral cam attaches to the posterior condyles of the femoral component, further facilitate cam clearance. The cam chamfers and relief groove cooperate in flexion to allow at least 12 degrees of rotation, both clockwise and counterclockwise, of the femoral component with respect to the tibial component around the axis of the spine.

1 Claim, 3 Drawing Sheets

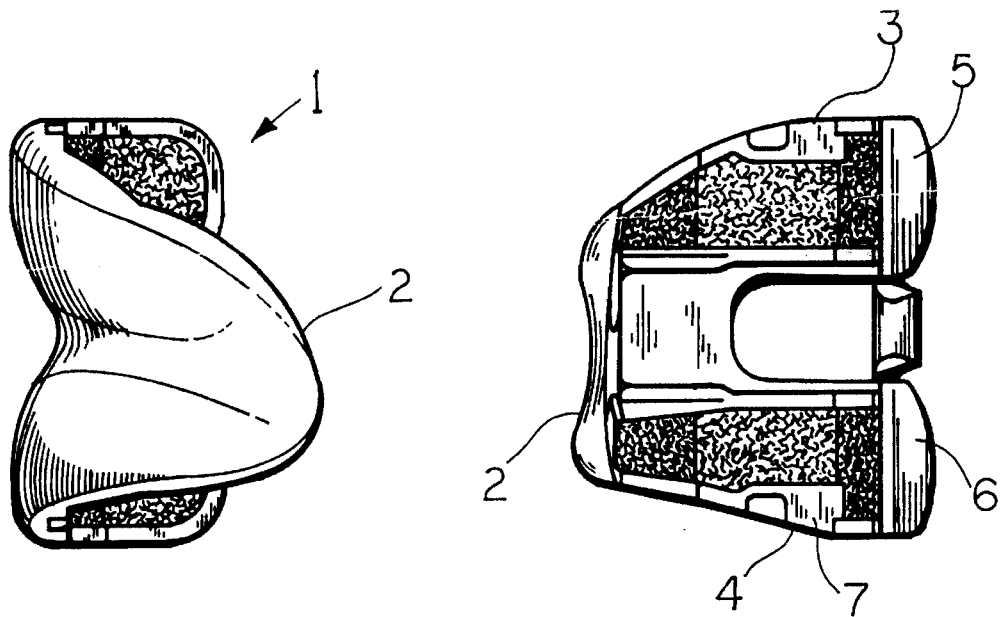
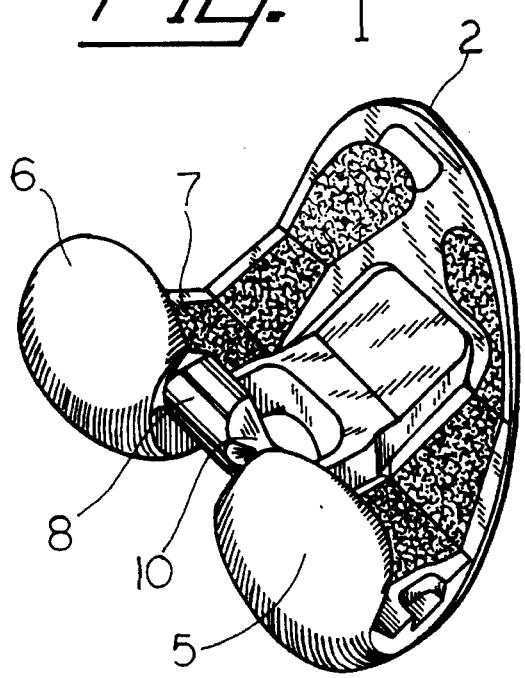
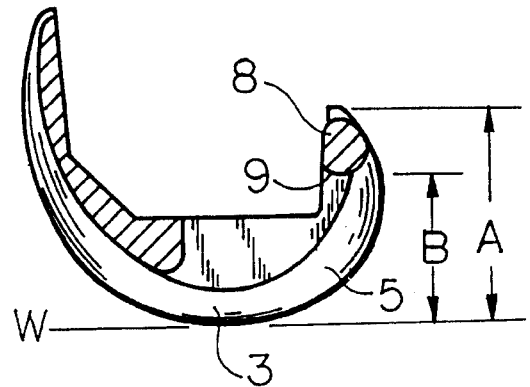

KNEE PROSTHESIS HAVING A TAPERED CAM

BACKGROUND OF THE INVENTION

The present invention relates to knee joint prostheses generally and to knee joint prostheses providing constrained articulation of the knee joint particularly.

A knee joint prosthesis typically comprises a femoral component (femoral) for replacing the surface of the femur at the knee joint, a tibial component (tibial) for replacing the corresponding tibial surface, and a patellar component for replacing the posterior surface of the patella. In a knee joint prosthesis intended to perform in the absence of functional cruciate ligaments, the femoral and tibial have complimentary geometries that limit the freedom of movement between the components to simulate the constraint and resulting motion normally provided by the ligaments.

A characteristic of normal knee motion is combined rotation and sliding of the femur with respect to the tibia during knee flexion. The rolling component of this motion results in the femur translating posteriorly with respect to the femur and is referred to as "rollback".

Another characteristic of normal knee motion is resistance to anterior displacement of the femur relative to the tibia in deep flexion. Such anterior displacement is referred to as anterior subluxation or anterior dislocation.

A representative and highly successful prior art knee prosthesis is taught in U.S. Pat. No. 4,298,992 granted to Burstein and Insall. That patent teaches a box-like recess between the condylar portions of the femoral having raised side walls extending from the anterior portion of the knee to the posterior portion of the knee and defining a box. A transverse convexly curved cam, integral with the box and forming a posterior boundary to the box, engages a concave surface on a spine extending from the tibial into the femoral box. To the extent that the spine extends into the femoral, bone must be resected to accommodate the spine and box.

This camming action forces the areas of contact between the tibial and femoral posteriorly, reproducing femoral rollback, to allow an increased range of flexion without impingement of the bone of the femur on the tibial component. The contact point between the cam and spine of prior art knees hits relatively high on the spine, thus requiring a large spine to resist the resulting shear and bending loads.

SUMMARY OF THE INVENTION

The present invention improves on prior knee prostheses by locating a cam on the femoral component between the posterior condyles and near the upper extreme of the condyles. With the cam located near the upper extreme of the posterior condyles, the cam contacts a tibial spine nearer its base than in prior prostheses. Low cam contact produces less shearing stress in the spine because the spine is thicker at its base. Thus low cam contact is less likely to result in shearing failure. Likewise, low cam contact results in a smaller rotational moment on the tibial. Because the spine is subject to less demanding forces, it is made smaller and therefore projects into the femoral to a lesser degree resulting in less necessary bone resection on the femur.

Also, since the cam is located near the upper extreme of the posterior condyles, as the knee is flexed, the contact point between the cam and spine remains near the base of the spine, even in deep flexion. This feature of the present invention causes it to remain resistant to anterior subluxation in deep flexion.

A relief groove formed in the tibial accommodates the femoral cam. This allows the cam to remain low on the tibial spine and even go below the edges of the tibial while maintaining adequate material in the tibial adjacent the relief groove.

Cam chamfers, where the femoral cam attaches to the posterior condyles, further facilitates cam clearance. The cam chamfers and relief groove also cooperate in flexion to allow at least 12 degrees of rotation, both clockwise and counterclockwise, of the femoral with respect to the tibial around the axis of the spine.

BRIEF DESCRIPTION OF THE DRAWINGS

FIG. 1 is a front view of the femoral component of the present invention.

FIG. 2 is top view of the femoral component of the present invention.

FIG. 3 is a perspective view of the femoral component of the present invention.

FIG. 4 is a side section view of the femoral component of the present invention.

DETAILED DESCRIPTION OF THE INVENTION

Figure 5:
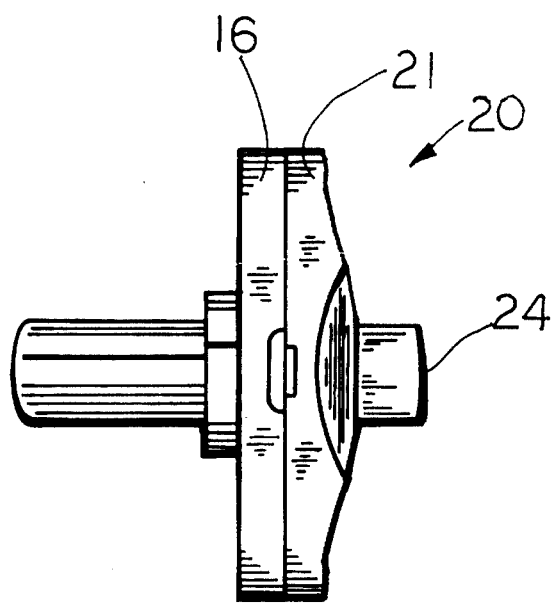
FIG. 5 is a front view of the tibial component of the present invention.
Figure 6:
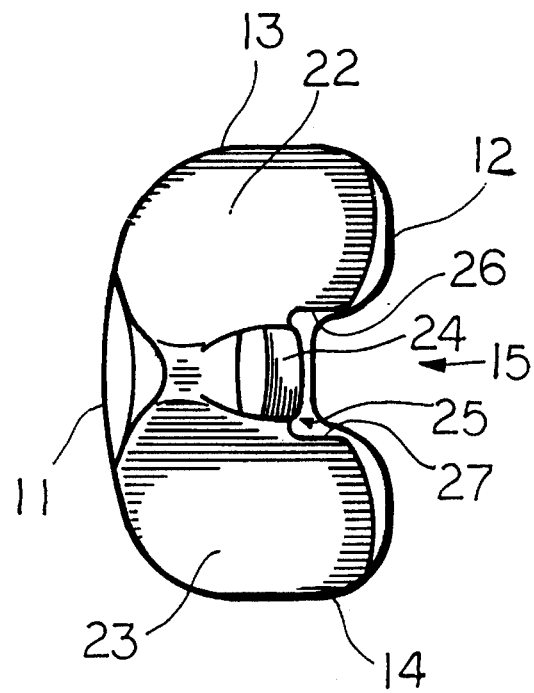
FIG. 6 is top view of the tibial component of the present invention.
Figure 7:
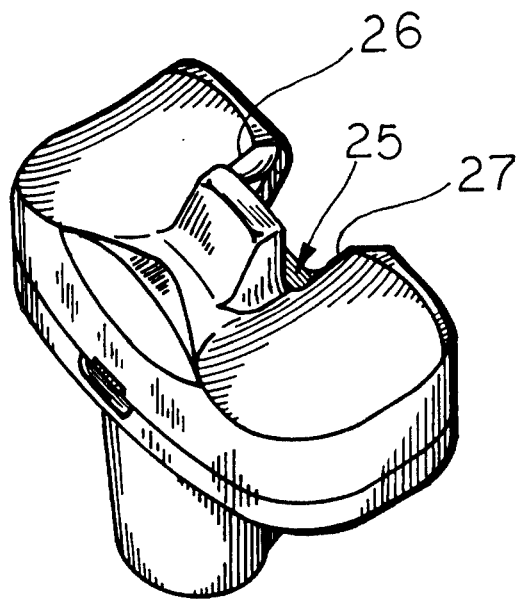
FIG. 7 is a perspective view of the tibial component of the present invention.
Figure 8:
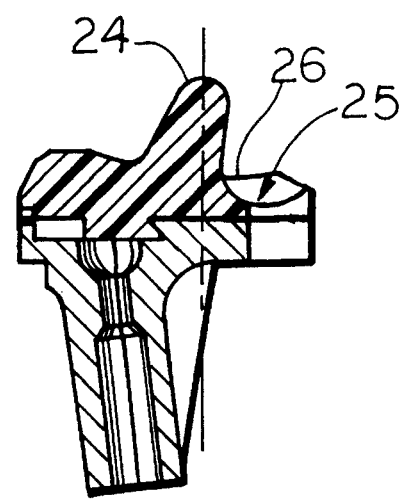
FIG. 8 is a side section view of the tibial component of the present invention.
Figure 9:
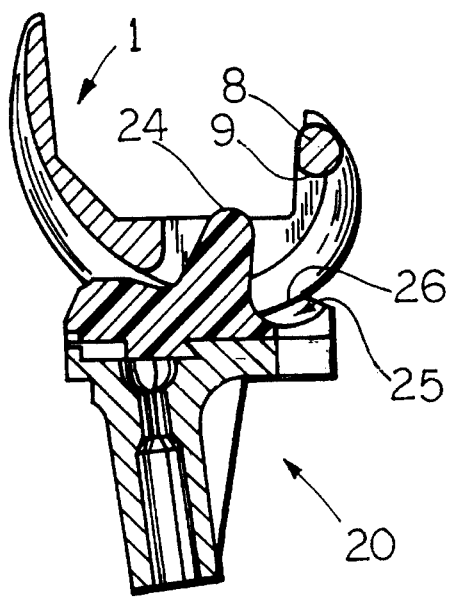
FIG. 9 is a side section view of the femoral and tibial components of the present invention articulating in approximately zero degrees of physiological flexion.
Figure 10:
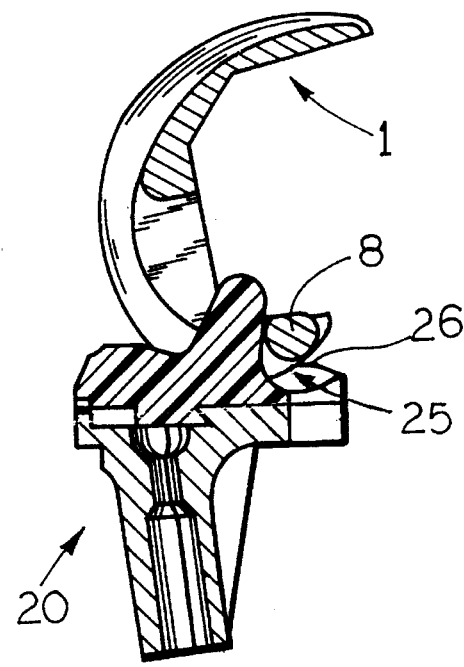
FIG. 10 is a side section view of the femoral and tibial components of the present invention articulating in approximately 75 degrees of physiological flexion.

Referring to FIGS. 1–12, a knee joint prosthesis includes a femoral component 1 comprising a pair of members joined anteriorly to form a patellar flange 2, the members being spaced distally to form a pair of distal condyles 3 and 4, and the members being spaced posteriorly to form a pair of posterior condyles 5 and 6. A horizontal femoral reference surface 7, defines the horizontal plane when the femoral 1 is in zero degrees of physiological flexion. Physiological flexion is used here to refer to the articulation of the knee joint in vivo and it ranges from zero to 120 degrees. A datum, W, corresponds to a plane tangent to the distal most portion of the distal condyles 3 and 4, and parallel to the horizontal femoral reference surface 7. The posterior condyles 5 and 6 reach a height A above datum W. A cam 8, having a spine engaging surface 9 along its lower extremity, extends between the posterior condyles 5 and 6. The cam 8 is located such that the spine engaging surface 9 is above the datum W a height B, B being at least 50% to 90% of the height A, preferably 66% to 69%. This range of heights corresponds to a range of sizes of femoral implants to accommodate different sizes of patients. In an exemplary medium sized femoral of the present invention, B is 69% of A. By comparison, in the prior art IB II knee prosthesis manufactured by Zimmer, Inc., B ranges from 42% to 44% of A.

The tibial 20 comprises a plate like body preferably having a tibial tray 16 and a plate like articular surface 21. The articular surface has anterior 11, posterior 12, medial 13 and lateral 14 sides. The articular surface 21 contains a pair of concave articular regions 22 and 23 formed in the medial 13 and lateral 14 sides for engaging the femoral condyles. A posterior notch 15 extends through the posterior side 12. This posterior notch allows the articular surface 21 to be used with a tibial tray 16 having a similar posterior notch. The posterior notch in the tibial tray 16 allows the tibial tray to be used with an articular surface designed for use where there is a functional cruciate ligament because the posterior notch accommodates the ligament. The ability of the tibial tray 16 to be used with cruciate ligament retaining articular surfaces as well as the cruciate ligament sacrificing articular surface 21 results in fewer parts being required in the implant system. A spine 24, having a longitudinal axis approximately perpendicular to the articular surface 21, projects above the articular regions 22 and 23 for engagement with the cam 8 of the femoral 1.

It is preferable to maintain as much material around the concave articular regions 22 and 23 as possible while accommodating the preferred low spine contacting cam described above. In the preferred embodiment this is accomplished by providing a tibial relief groove 25 and femoral cam chamfers 10. The tibial relief groove 25 extends partially through the posterior side 12 and is adjacent to and extends between the concave articular regions 22 and 23. The tibial relief groove 25 is adapted to closely receive the cam 8 when the knee is in flexion with a minimum removal of tibial material.

Figure 11:
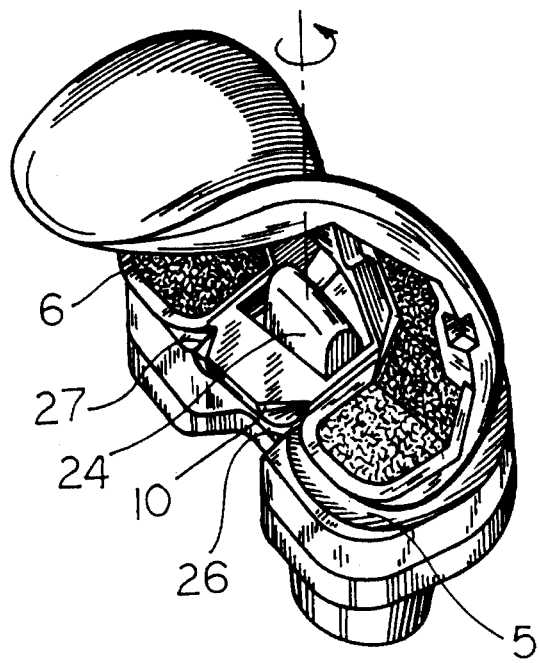
FIG. 11 is a perspective view of the femoral and tibial components of the present invention articulating in flexion showing the femoral component rotated approximately 12 degrees about the tibial spine.
Figure 12:
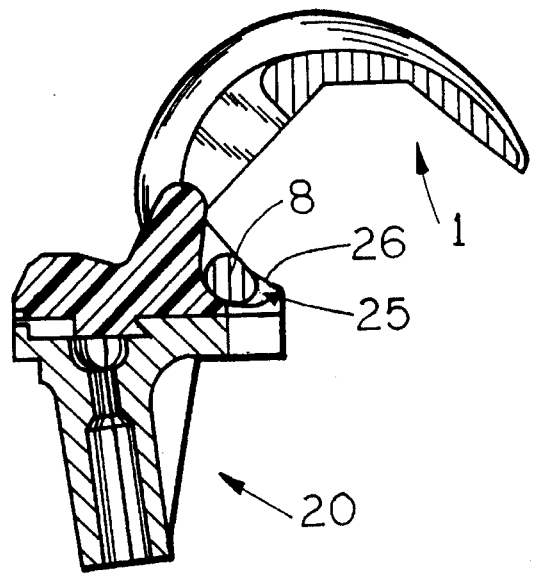
FIG. 12 is a side section view of the femoral and tibial components of the present invention articulating in approximately 120 degrees of physiological flexion.

As seen in FIGS. 3 and 11, the body of the cam tapers from its intermediate portion to each of the posterior condyles 5 and 6 to form the femoral cam chamfers 10. Therefore, the intermediate portion of the cam has a greater cross-sectional area than the chamfered portions of the cam adjacent the condyles. The femoral cam chamfers 10 allow the edges 26 and 27 of the concave articular regions 22 and 23 to rise higher and support articulation. Without the femoral cam chamfers 10 the edges 26 and 27 would have to be lower.

When the cam 8 and tibial relief groove 25 are in engagement, the femoral cam chamfers 10 and the tibial relief groove 25 cooperate to allow a minimum of twelve degrees of rotation, both clockwise and counterclockwise, of the femoral 1 with respect to the tibial 20 around the axis of the spine 24, as shown in FIG. 11.

It will be understood by those skilled in the art that the foregoing has described a preferred embodiment of the present invention and that variations in design and construction may be made to the preferred embodiment without departing from the spirit and scope of the invention defined by the appended claims.

What is claimed is:

1. In combination:

a femoral component of a knee joint prosthesis comprising a pair of members joined anteriorly to form a patellar flange, the members being spaced distally to form a pair of distal condyles, and the members being spaced posteriorly to form a pair of posterior condyles, the posterior condyles reaching a height A above a datum W, the datum W corresponding to a plane tangent to the distal most portion of the distal condyles and being horizontal when the femoral is in zero degrees of physiological flexion, a cam extending between and attaching to the posterior condyles, the cam having a spine engaging surface along its lower extremity, the cam being located such that the spine engaging surface is located a height B above the datum W, the height B being from 66% to 69% of the height of A, the cam tapering from an intermediate portion to each of the posterior condyles to form femoral cam chamfers such that the intermediate portion has an intermediate cross sectional area at a point between the posterior condyles that is greater than a cross sectional area of the cam adjacent one of the posterior condyles, the cam being located between the condyles so that it is contained between the anterior most and posterior most aspects of the posterior condyles such that the cam does not project anteriorly beyond the anterior most aspect of the posterior condyles and the cam does not project posteriorly beyond the posterior most aspect of the posterior condyles; and a tibial component of a knee joint prosthesis comprising a plate like body having anterior, posterior, medial and lateral sides, the body having a pair of concave articular regions formed in the medial and lateral sides, the body having a posterior notch extending through the posterior side, the body having a tibial relief groove extending partially through the posterior side and extending between the concave articular regions, a spine projecting from the body between the articular regions, the tibial relief groove being adapted to receive the cam when the knee is in flexion and the relief groove and femoral cam chamfers cooperating to allow a minimum of twelve degrees of rotation, both clockwise and counterclockwise, of the femoral component with respect to the tibial component around the axis of the spine when the cam is received in the relief groove.

* * * * *